United States Patent [19]
Corbett

[11] 3,983,203
[45] Sept. 28, 1976

[54] METHOD OF MAKING A CATHETER WITH AN INTEGRAL LUER LOCK MEANS

[75] Inventor: Joseph H. Corbett, Glens Falls, N.Y.

[73] Assignee: Sherwood Medical Industries Inc., St. Louis, Mo.

[22] Filed: Nov. 16, 1973

[21] Appl. No.: 416,722

[52] U.S. Cl. .............................. 264/150; 264/159; 264/161; 264/177 R; 264/209; 264/210 R; 264/250; 264/296; 264/322
[51] Int. Cl.² ................ B29C 17/14; B29D 23/04; B29F 3/00; B29F 5/00
[58] Field of Search .......... 264/150, 161, 167, 292, 264/296, 322, 320, 294, 250, 209, 210, 159, 177 R, 210 R; 425/806; 83/94; 285/423; 128/214.4, 214

[56] References Cited
UNITED STATES PATENTS

| | | | |
|---|---|---|---|
| 2,743,478 | 5/1956 | Harlow et al. | 425/806 |
| 2,922,667 | 1/1960 | Lanciano | 285/260 |
| 2,940,126 | 6/1960 | Sheridan | 264/167 |
| 3,270,117 | 8/1966 | Hobson | 425/393 |
| 3,461,761 | 8/1969 | Mojonnier | 83/914 |
| 3,497,582 | 2/1970 | Petterson | 264/209 |
| 3,649,150 | 3/1972 | Gilbert | 264/98 |
| 3,674,404 | 7/1972 | Burlis et al. | 264/176 R |
| 3,734,095 | 5/1973 | Santomieri | 128/214.4 |
| 3,751,541 | 8/1973 | Hegler | 264/150 |
| 3,783,241 | 1/1974 | Uhlig | 425/806 |

FOREIGN PATENTS OR APPLICATIONS

| | | | |
|---|---|---|---|
| 639,997 | 7/1950 | United Kingdom | |
| 293,653 | 11/1971 | U.S.S.R. | 264/161 |

*Primary Examiner*—Willard E. Hoag
*Attorney, Agent, or Firm*—S. N. Garber; W. R. O'Meara

[57] ABSTRACT

The method of making a catheter with integral Luer locking means including extruding plastic material to form a tube having a relatively thin-walled portion of relatively small diameter and a relatively thick-walled portion of relatively large diameter. The tube is inserted into a heat forming mold having a Luer lock forming portion, and a mandrel, having a Luer taper, is forced into the portion of large diameter to heat form an integral catheter connector portion with an internal taper and an integral external flange having Luer locking lugs adapted for locking engagement with a complementary Luer lock connector. The catheter can be used in a intravenous catheter or cannula placement unit.

6 Claims, 9 Drawing Figures

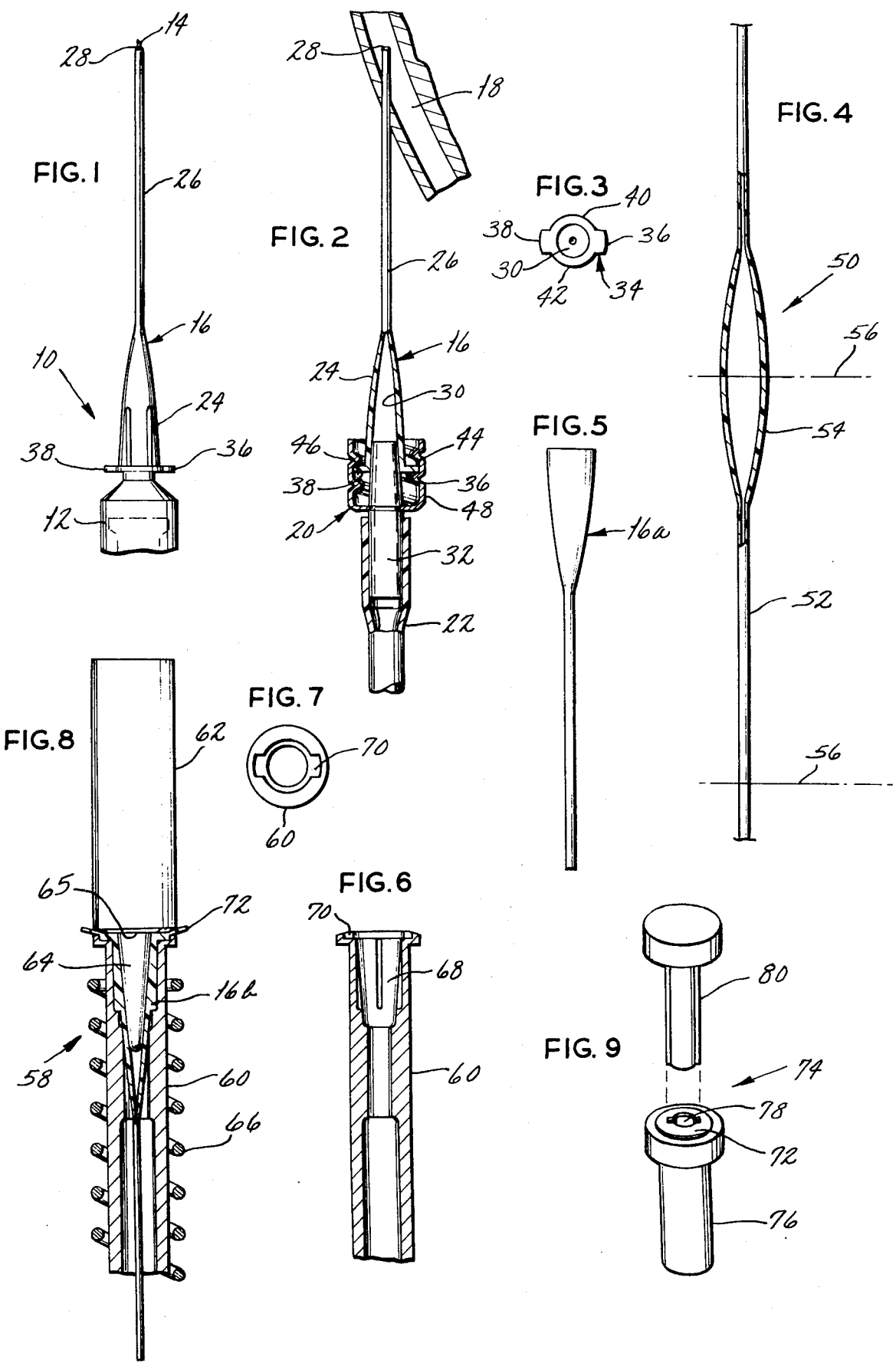

METHOD OF MAKING A CATHETER WITH AN INTEGRAL LUER LOCK MEANS

BACKGROUND OF THE INVENTION

This invention relates to the method of making catheters and more particularly to the method of making a catheter having integral Luer locking means thereon.

Intravenous catheter placement units, for example, generally include a syringe with a hypodermic needle and a plastic catheter or cannula disposed on the needle. The plastic cannula for such a unit usually has a conical or Luer tapered connector at the proximal end, and a main catheter portion of relatively smaller diameter connected to the connector. The connector portion and main catheter portion may be economically and inseparably connected by integrally forming them to form a single-piece cannula. As is well known, the distal ends of the needle and cannula in such a unit are inserted into a body vessel, such as a vein, and proper placement of the cannula verified by effecting aspiration of blood into the syringe. The syringe and needle are then removed from the cannula, and, where infusion of fluid is to take place, a tube or infusion catheter having a male Luer connector is connected to the connector portion of the cannula to effect a Luer slip fit. While a Luer slip connection between the intravenous cannula and tubing is generally reliable, it is often desirable or necessary to have a Luer locking connection to positively insure against separation and leakage of fluid under many conditions of use, for example, where the catheter is to be used in critical situations or over a relatively long period of time, such as during infusion of a liquid. Some cannulas have been provided with Luer locking flange means at the proximal connector end thereof for this reason, however, there have been certain undesirable aspects associated with the manufacture of such cannulas. Two-piece catheters have been made in which the main portion of small diameter is extruded and a separate injection-molded Luer lock connector attached, such as by an adhesive. However, this method was relatively expensive and there was the possibility of the pieces separating under fluid pressure conditions. Also, single-piece catheters having an integral Luer lock connector have been made by the injection molding process but it has been difficult to obtain cannula walls which are thin enough in the distal or insertion portions of the catheter and which provide the desired flexibility, especially in the smaller sizes, such as 16, 18 and 20 gauge catheters. This tends to cause trauma and tends to undesirably affect the flexibility, handling, and flow characteristics of the catheter. Also, the injection molding process does not lend itself to the production of catheters or tubing of relatively long lengths because of the requirement of a correspondingly relatively long and costly mold.

SUMMARY OF THE INVENTION

Accordingly, it is an object of the present invention to provide a novel method of making plastic catheters having an integral connector portion of the Luer lock type which has sufficient wall thickness for good rigidity, and a main portion having good flexural characteristics throughout its length.

Another object is to provide a method of making a catheter having an integral Luer lock connector which may have any desired length and yet be economical to make.

Another object is to provide a novel method of making a plastic cannula having an integral Luer lock connector portion having relatively thick walls, and a main portion with relatively thin walls and a relatively narrow diameter, and which avoids the above-mentioned undesirable aspects associated with the process of injection molding and the two-piece process.

In accordance with the present invention, a method of making a plastic catheter having integral Luer lock means includes the steps of forming, by extruding plastic material, a tube having a portion with a relatively small diameter, and a portion with a relatively large diameter, and heat forming the portion of relatively large diameter to provide Luer lock means thereon.

These as well as other objects and advantages of the present invention will become apparent from the following detailed description and accompanying drawing in which corresponding reference characters indicate corresponding parts.

BRIEF DESCRIPTION OF THE DRAWINGS

FIG. 1 is a partial elevational view of an intravenous catheter placement unit with a cannula made in accordance with the present invention;

FIG. 2 is a cross-sectional elevational view showing the cannula of FIG. 1 connected in a system for transferring fluids between tubing and a body vessel;

FIG. 3 is a bottom end view of the cannula shown in FIGS. 1 and 2;

FIG. 4 illustrates an extrusion step in the method of making the cannula of FIG. 1;

FIG. 5 is a elevational view of a portion of the extruded tubing of FIG. 4;

FIG. 6 is a vertical cross-sectional view of a heat forming mold used in performing a molding step;

FIG. 7 is an upper plan view of the mold of FIG. 6;

FIG. 8 is a cross-sectional elevational view illustrating a forming step utilizing the mold of FIG. 6; and FIG. 9 is a perspective view on a reduced scale, of punch and die apparatus for removing excess material from the part produced by the molding step of FIG. 8.

DESCRIPTION OF THE PREFERRED EMBODIMENT

Referring now to the drawings, there is shown in FIG. 1 a catheter placement unit 10 including a syringe 12 having a needle cannula or hypodermic needle 14 connected thereto, and a plastic catheter or cannula 16 removably disposed on needle 14 and which is made in accordance with the present invention. Cannula 16 is used as an intravenous catheter or cannula which is adapted to be inserted into a body vessel while on the needle 14. In utilizing the unit 10, the distal ends of needle 14 and cannula 16 are inserted into a body vessel, aspiration of blood into a portion of the syringe is effected to verify proper placement, and then the needle and syringe are removed from the inserted cannula. In FIG. 2, the cannula 16 is shown disposed in a body vein 18 and connected through a Luer lock connecting member 20 which may be of conventional design, to plastic tubing 22. Tubing 22 is secured at one end, such as by a suitable adhesive, to the connecting member 20, and is connected at the other end to a source or container of infusion fluid (not shown) so that infusion fluid will flow through tube 22, connecting member 20, and cannula 16 to vein 18.

The cannula 16 has a tapered or conically shaped connector portion 24 at the proximal end which is integrally connected with a main cannula portion 26 that extends to the distal end of the cannula. Portion 26 has a much smaller diameter than connector portion 24 and it has a distal tip 28 which is further tapered for easy insertion into the vein. The connector portion 24 of the cannula has an internal conical or Luer tapered bore 30 which receives a plastic, Luer tapered, male fluid coupling member 32 of Luer lock connecting member 20 that has a bore extending through it.

As seen also in FIG. 3, the proximal end of cannula 16 is provided with a radially outwardly extending annular flange 34 including a pair of diametrically opposed, radially outwardly extending lugs 36 and 38 which extend for a minor portion of the circumference of the proximal end of the cannula and which are shown in the same plane with each other. Flange 34 also has opposed ridge portions 40 and 42 between the lugs 36 and 38 which extend radially outwardly to a lesser extent than the lugs. The lugs 36 and 38 serve as external Luer lock members or thread segments which are respectively received in a pair of internal threads 44 and 46 of an internally threaded coupling element or hub 48 of Luer lock connecting member 20. Hub 48 is shown formed of metal and is secured to the male connector member 32 such as by a friction fit or other suitable means. The threads 44 and 46 start at points 180° apart so that Luer lock lugs 36 and 38 on the cannula enter the threads when the cannula is inserted into the open end of hub 48.

Upon relative rotation of the cannula 16 and connecting member 20 in the proper direction, the internal threads cause the cannula 16 to move into the hub 48 with coupling member 32 moving into the conical or Luer taper bore 30 of the cannula to form a Luer slip-fit, fluid tight connection. Generally, in making this fluid tight connection the coupling member 32 and the cannula connector portion 24 are grasped and manually twisted or rotated relatively in opposite directions until a significant resistance to turning is effected. This use requires that the connector portion 24, as well as the lugs 36 and 38, be of substantial rigidity to enable a reliable fluid tight connection to be made with the connecting member 20 and to prevent separation during use. Thus, the side walls of the connector portion 24 must be sufficiently thick to obtain the desired or necessary rigidity.

In the case of catheter placement cannula 16, the main portion 26 must be of smaller diameter and have walls which are relatively thin because the distal portion is to be inserted into a patient, while the connector portion 24 must have relatively thick walls for rigidity.

The present invention concerns a method of making cannulas, such as cannula 16, which avoids injecting molding. In making the cannula 16, plastic, such as polypropylene, is extruded in the form of tubing 50, as shown in FIG. 4. This extruded tubing includes a relatively long portion 52 of relatively small diameter and with thin walls, and a bubble or a generally conically ended portion 54 of relatively large diameter with relatively thick walls. The extruded tube 50, after being cooled, is cut to size such as by cutting it through at locations indicated by lines 56 to provide an extruded tube section 16a, as shown in FIG. 5. The tube section 16a is then placed in heat forming apparatus illustrated in FIGS. 6–8 to be heat formed, as will be more fully explained hereinafter.

A process by which the extruded tubing 50 is provided, is disclosed in U.S. Pat. No. 3,674,404, issued July 4, 1972, and assigned to the same assignee as this application. Briefly, the method includes delivering molten plastic from an extruder operating at a constant speed to an extrusion die with an injector-accumulator disposed in the molten plastic flow path for periodically injecting and withdrawing molten plastic flowing from the extruder to thereby vary the thickness of the walls of the resulting extrusion. The injector-accumulator may include a cylinder and a selectively controlled reciprocating piston which withdraws plastic from the flow path and accumulates it to produce an extrusion with thin walls, and injects accumulated plastic into the path to produce an extrusion having relatively thick walls. Air is injected into the extrusion die and into the tube lumen to vary the internal diameter and contour of the tube as desired. Thus, by programming the inject and withdrawal phases of the injector-accumulator with the injection of air, tubing such as shown in FIG. 4 is readily obtained. For a further detailed description of a method and apparatus for producing tubing having walls which vary in thickness and portions which vary in diameter, reference should be made to the above mentioned patent.

The tubing section 16a is to be formed by a mold and mandrel heat forming apparatus indicated generally at 58 in FIG. 8. The apparatus 58 includes a lower mold portion 60, shown also in FIG. 6 and 7, for receiving the tube 16a, a mandrel 62 which includes a conical or Luer tapered forming portion 64 for insertion into the tube 16a and mold 60, and a flange forming radial shoulder 65, and heating or induction coils 66 for connection with a suitable source of electric energy for heating the apparatus to soften the plastic tube.

The upper portion of mold 60 has a cavity 68 with walls that, in association with the mandrel 62 during the molding operation, form the conical, ribbed connector portion 24 in the finished cannula as seen in FIG. 1. Also, the upper end of mold 60 is provided with a Luer lock flange forming cavity indicated generally at 70 as best seen in FIG. 7 which, during forming, provides the flange 34 including Luer lock lugs 36 and 38, as best seen in FIG. 3.

In heat forming the tube 16a, it is inserted into the lower mold 60 with a portion at the upper enlarged end extending above the upper surface of the mold and with the coils 66 heating the mold and tube. The mandrel is then lowered with the tapered lower portion 64 entering the tubular portion of tube 16a and effecting a flowing of plastic material to form the inner Luer tapered surface 30 of the finished cannula, the Luer locking flange 34 and an annular excess portion or flash indicated at 72 in FIG. 8. The thermoformed plastic tubing, which is indicated at 16b in FIG. 8, is removed from the mold by separating the mold and mandrel, and allowed to cool. The annular excess portion 72 of the formed tube 16b is then removed, for example, by a suitable punch and die set, such as indicated at 74 in FIG. 9. The set includes a die 76 having an upper opening 78 with a periphery conforming to the outer periphery of the finished flange 34 (FIG. 3), and a punch 80 having a bottom surface with a periphery complementary to the periphery of opening 78. In detaching the excess plastic 72, the tube 16b is inserted into the die 76 and properly oriented with respect to opening 78. The punch 80 is then moved downwardly into opening 78, with the finished cannula 16 (FIG. 1) moving downwardly and out of the die 76 with the excess material 72 remaining.

Where a beveled end 28 is to be formed, a rod of proper diameter is inserted into the finished cannula, and, using sufficient heat, drawing and thinning the tip to reduce its outer diameter. This latter step may include cutting off portions of the thinned tip to proper length.

From the foregoing, it will be apparent that the method of making cannulas, such as the method of making cannula 16, avoids the usual injection molding process and its disadvantages while providing a relatively economical method of making a cannula having good characteristics, such as a high degree of rigidity in the Luer lock connector portion, and good flexibility in the insertion portion which has a narrow outer diameter.

The method described herein readily lends itself to the manufacture of other types of plastic catheters or cannulas which are used for purposes other than intravenous insertion. For example, plastic tubing and catheters for drainage, suction, feeding, and other purposes including general purpose tubing, may be advantageously made by the process of the present invention. Thus, cannulas, catheters and tubing having integral Luer lock connector flanges or lugs may be relatively economically made of any desired length, for example, 5 feet, by the method disclosed herein. The manufacture of relatively long catheters or cannulas is not economically feasible with injection molding processes since such processes generally require a mold having a length equal to that of the finished catheter.

In view of the above, it will be seen that the several objects of the invention are achieved and other advantageous results obtained. As various changes could be made in the above disclosure without departing from the scope of the invention, it is intended that all matter in the above description or shown in the company drawings shall be interpreted as illustrative and not in a limiting sense.

What is claimed is:

1. A method of making a single piece plastic catheter having, at one end of the catheter, an integrally formed Luer lock connector having radially outwardly extending lug means thereon, and a tapered bore with walls tapering radially inwardly toward the opposite end of the catheter, for connection with complementary Luer lock connecting means of another member comprising the steps of extruding thermoplastic tubing having a first portion and a second portion integral with said first portion and axially disposed therefrom, said second portion having a smaller outer diameter than said first portion and a wall thickness less than that of said first portion, whereby said second portion is more flexible than said first portion; cutting said tubing to provide a tube of selected length which includes at least a part of each of said first and second portions with a part of said first portion at one end of the tube; inserting an end portion of said tube having a part of said first portion in a mold having an axially extending cavity and a radially extending cavity at one end of said axially extending cavity, heating said end portion of said tube and inserting a tapered mandrel into said end portion, reshaping said end portion to conform to said tapered mandrel, and causing some of the thermoplastic material to move into said radially extending cavity to form said lug means on said end portion.

2. The method of claim 1 including removing said tube from said mandrel and said mold.

3. The method of claim 1 wherein said thermoplastic tubing includes polypropylene.

4. The method of claim 1 including the additional steps of causing excess thermoplastic material to move between said mandrel and said mold and removing said excess material from said tube.

5. The method of claim 4 including inserting the end of said tube having said Luer lock connector into a die and moving a punch into said die to cut off said excess thermoplastic material.

6. A method of making a single piece plastic catheter having, at one end of the catheter, an integrally formed Luer lock connector having radially outwardly extending lug means thereon, and a tapered bore with walls tapering radially inwardly toward the opposite end of the catheter, for connection with complementary Luer lock connecting means for another member comprising the steps of extruding thermoplastic tubing having a first portion and a second portion integral with said first portion and axially disposed therefrom, said second portion having a smaller outer diameter than said first portion and a wall thickness less than that of said first portion, whereby said second portion is more flexible than said first portion, cutting said tubing to provide a tube of selected length which includes at least a part of each of said first and second portions with a part of said first portion at one end of the tube; inserting an end portion of said tube having a part of said first portion in a mold having an axially extending cavity and two circumferentially spaced, diametrically opposed, radial cavities at an end of said axially extending cavity, heating said end portion of said tube and inserting a tapered mandrel into said end portion and reshaping said end portion to conform to said tapered mandrel, causing some of the thermoplastic material to move into said radial cavities to form said lug means on said end portion, moving excess thermoplastic material between said mandrel and said mold forming flash connected to said tube, removing said tube from said mandrel and said mold, and removing said flash from said tube.

* * * * *